United States Patent [19]

Spies

[11] 4,258,035

[45] Mar. 24, 1981

[54] METHOD AND COMPOUND FOR TREATMENT OF ARTHRITIC CONDITIONS IN DOGS

[76] Inventor: Janice A. Spies, 335 Brookside Cir., Wheaton, Ill. 60187

[21] Appl. No.: 964,332

[22] Filed: Nov. 27, 1978

[51] Int. Cl.³ ............................................. A61K 35/78
[52] U.S. Cl. .................................................... 424/195
[58] Field of Search ........................................ 424/195

[56] References Cited

PUBLICATIONS

Clarke, "A Dictionary of Practical Materia Medica", published by The Homoeopathic Pub. Co., London (1900), pp. 727–729, 1130–1132, 1340–1343, 1482 to 1485 & 1526–1530.

*Primary Examiner*—Stanley J. Friedman
*Attorney, Agent, or Firm*—John C. Brezina; John H. Shurtleff

[57] ABSTRACT

The invention is:

A composition composed of Comfrey, Mullein, Fenugreek, Nettle, Broom Tops, Boneset, herbal plants occurring in nature which may be cultivated. This composition when added to the regular food of dogs, has alleviated symptoms of arthritic spinal conditions in dogs.

4 Claims, No Drawings

METHOD AND COMPOUND FOR TREATMENT OF ARTHRITIC CONDITIONS IN DOGS

This invention relates to a combination of powders made from certain herbs which are combined in certain portions and fed to the animal with their food. Symptoms of arthritic conditions in dogs as evidenced by calcification of the spine have been alleviated and improvements have been shown by X-rays taken at the onset of treatment and several months later after treatment.

The compound of the invention is composed of six basic ingredients: (a) Comfrey (*Symphytum officinale*); (b) Mullein (*Verbascum thapsus*); (c) Fenugreek (*Trigonella foenumgraecum*); (d) Nettle (*Urtica dioica*); (e) Broom tops (*Cytisus scoparius*); and (f) Boneset (*Eupatorium perfoliatum*).

These herbal components are used in the form of powders which are made from the root of the Comfrey plant, the leaf of the Mullein plant, the seed of the Fenugreek plant, and the pulverized dried Nettle, Broomtops and Boneset plants.

This combination of herbal powders is added to the dogs' food once a day. The proportions of the ingredients in a preferred embodiment, for large dogs such as St. Bernards and Great Danes, are Comfrey 1.8 grams; Mullein 0.6 grams; Fenugreek, Nettle and Boneset 0.3 grams and Broom tops 0.25 grams.

For small dogs, on the order of 10 lbs., a preferred embodiment is 25% of the above amounts; for dogs of intermediate size the amounts are proportional to the above amounts depending on the weight of the dog.

The approximate proportions in parts by weight are therefore as follows: 1.8 parts (a) Comfrey; 0.6 parts (b) Mullein; 0.3 parts each of (c) Fenugreek, (d) Nettle and (f) Boneset; and 0.25 parts by (e) Broom tops. The daily unit dosage of the powdered composition according to the above figures range from above 0.9 grams for the small dogs up to 3.55 grams for the largest dogs.

The following are examples of use of the compound of the the invention.

EXAMPLE 1

A three year old Great Dane had a very pronounced arthritic condition and was seriously incapacitated. X-Rays showed pronounced arthritic deposits at the interface of the joints of the dogs spine. After two months of treatment of the abovementioned formulation for large dogs, a noticeable change could be discerned from X-Rays. Areas of the deposits between the joints which appeared relatively solid white in the initial X-Rays became greyer showing demineralization of the calcification. In a third X-Ray taken four months after the treatment began, the deposits showing existence of the arthritic condition had significantly disappeared.

EXAMPLE 2

A ten year old German Shepard was given a daily dosage of 50% of the aforementioned preferred embodiment for the large dogs. At the onset of the treatment the dog could not get up on her end. X-Rays showed that the spine was substantially fused with substantial amounts of calcification between the joints. After three and a half months of treatment with the applicant's formulation, the dog's mobility improved substantially and X-Rays which had formerly had shown deposits between the joints appearing in white showed up significantly darker indicating that calcification had been reduced.

EXAMPLE 3

A six year old Great Dane had an arthritic condition that was so severe that the dog could no longer walk without falling. After five months treatment with the formulation set forth above for large dogs, the dog could walk normally and X-Rays showed that deposits between the joints had been reduced.

I claim as my invention:

1. The method of reducing calcification of the spine as an arthritic condition in dogs, said method comprising feeding a dog having said condition a powdered mixture of herbal components consisting essentially of:
   (a) Comfrey as *Symphytum officinale;*
   (b) Mullein as *Verbascum thapsus;*
   (c) Fenugreek as *Trigonella foenumgraecum;*
   (d) Nettle as *Urtica dioica;*
   (e) Broom tops as *Cytisus scoparius;* and
   (f) Boneset as *Eupatorium perfoliatum,*
the powders being made from the root of said Comfrey plant, the leaf of said Mullein plant, the seed of said Fenugreek plant and the pulverized dried plans of said Nettle, Broom tops and Boneset, said powders being combined in the proportions of about 1.8 parts of (a), 0.6 parts of (b); 0.3 parts each of (c), (d) and (f); and 0.25 parts of (e).

2. The method as claimed in claim 4 wherein the daily unit dosage being fed to the dog ranges from about 0.9 grams for small dogs of about 10 pounds in weight up to about 3.55 grams for the largest dogs.

3. A composition for reducing calcification of the spine as an arthritic condition in dogs, said composition consisting essentially of the following components in powder form:
   (a) Comfrey as *Symphytum officinale;*
   (b) Mullein as *Verbascum thapsus;*
   (c) Fenugreek as *Trigonella foenumgraecum;*
   (d) Nettle as *Urtica dioica;*
   (e) Broom tops as *Cytisus scoparius;* and
   (f) Boneset as *Eupatorium perfoliatum,*
the powders being made from the root of said Comfrey plant, the leaf of said Mullein plant, the seed of said Fenugreek plant and the pulverized dried plants of said Nettle, Broom tops and Boneset, said powders being combined in the proportions of about 1.8 parts of (a), 0.6 parts of (b); 0.3 parts each of (c), (d) and (f); and 0.25 parts of (e).

4. A composition as claimed in claim 3 in the form of a daily unit dosage of from about 0.9 grams for small dogs up to about 3.55 grams for the largest dogs.

* * * * *